(12) United States Patent
Alravvi et al.

(10) Patent No.: US 11,559,326 B2
(45) Date of Patent: Jan. 24, 2023

(54) DISPOSABLE CIRCUMCISION APPARATUS AND METHOD OF USE OF THIS APPARATUS

(71) Applicant: Omar Alravvi, Fatih/Istanbul (AR)

(72) Inventors: Omar Alravvi, Fatih/Istanbul (TR); Abu-Baker Omar Mahmood Al-Rawe, Fatih/Istanbul (TR); Othman Omar Mahmood Al-Rawe, Fatih/Istanbul (TR)

(73) Assignee: Omar Alravvi, Fatih/Istanbul (TR)

( * ) Notice: Subject to any disclaimer, the term of this patent is extended or adjusted under 35 U.S.C. 154(b) by 53 days.

(21) Appl. No.: 16/322,902

(22) PCT Filed: Aug. 1, 2017

(86) PCT No.: PCT/TR2017/050362
§ 371 (c)(1),
(2) Date: Feb. 1, 2019

(87) PCT Pub. No.: WO2018/067090
PCT Pub. Date: Apr. 12, 2018

(65) Prior Publication Data
US 2019/0167292 A1    Jun. 6, 2019

(30) Foreign Application Priority Data
Aug. 2, 2016 (TR) .................. 2016/10821

(51) Int. Cl.
*A61B 17/326* (2006.01)
*A61B 17/28* (2006.01)
*A61B 17/00* (2006.01)

(52) U.S. Cl.
CPC .... *A61B 17/326* (2013.01); *A61B 2017/0023* (2013.01); *A61B 2017/2829* (2013.01)

(58) Field of Classification Search
CPC ...................... A61B 17/326; A61B 2017/2829
See application file for complete search history.

(56) References Cited

U.S. PATENT DOCUMENTS 2,747,576 A * 5/1956 Bronstein ............ A61B 17/326
606/118
3,566,873 A * 3/1971 Melges ................ A61B 17/326
606/118

(Continued)

FOREIGN PATENT DOCUMENTS

| CN | 203988303 U | 12/2014 |
| FR | 3028748 A1 | 5/2016 |
| WO | WO 2018/067090 A4 | 4/2018 |

*Primary Examiner* — Katherine M Shi
*Assistant Examiner* — Mohammed S Adam
(74) *Attorney, Agent, or Firm* — Maier & Maier, PLLC

(57) ABSTRACT

New disposable system devises and procedure for circumcision. The new procedure is by using the clamp in the same way of using bone cutter forceps, the penis marked by skin marker below the level of coronal sulcus, the prepuce retracted, a glans protector probe introduced above the glans, the prepuce pulled back over the probe, grasped by fingers on the probe to have painless holding. The modified bone cutter with blind cut end and groove on the upper surface is applied on the level of the skin mark. Light pressure separates the glans protector from its handle, then strong pressure on prepuce applies by this modified bone cutter, a sharp knife cuts the prepuce above the instrument, left a skin tag in the groove of the instrument, a heated oval shape stainless steel coated cupper cautery pass above the grove, the heating is by gas or electricity, but the electrical current must be cut off before application, the temperature between 140-300, glans protector removed no need for any dressing. Another modification is the removable disposable heads of the bone cutter. The result is very rapid circumcision with the lowest complication specially bleeding.

4 Claims, 16 Drawing Sheets

(56) References Cited

U.S. PATENT DOCUMENTS

| | | | |
|---|---|---|---|
| 3,678,935 A | 7/1972 | Bronstein | |
| 5,269,788 A * | 12/1993 | Nelson, III | A61B 17/326 24/531 |
| 2010/0114112 A1 * | 5/2010 | Mansour | A61B 17/326 606/118 |
| 2018/0206876 A1 * | 7/2018 | Souaida | A61B 17/326 |

* cited by examiner

Figure 6a                    Figure 6b

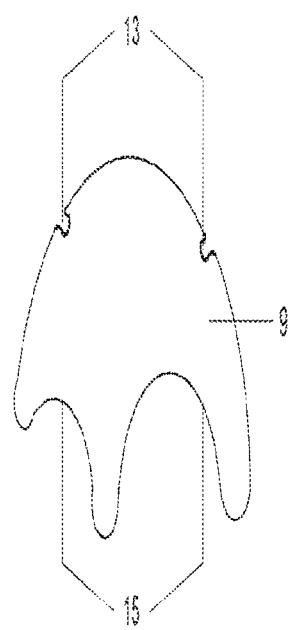
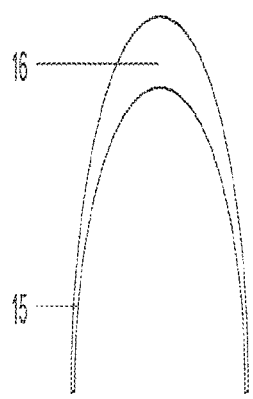
Figure 8a                    Figure 8b

DISPOSABLE CIRCUMCISION APPARATUS AND METHOD OF USE OF THIS APPARATUS

TECHNICAL FIELD

This invention is related to a disposable circumcision apparatus, the use of which allows that the circumcision procedure is completed in about one and half minute and there is no bleeding during the procedure, which does not require any anesthesia since the period in which the pain is felt is too short because the pain starts with a strong constriction effect of the bone cutter and ends within about ten seconds until the foreskin is removed, which does not require any dressing because the skin is attached to the mucosa and, that there is no open wound or hole, which ensures a very quick recovery since there is no gap between the mucosa and the foreskin due to the strong pressure that pushes the porous tissue and, makes the skin end closer to the end of the mucosa, and which requires only one person to use, and to the method of use of this apparatus.

BACKGROUND

Circumcision is a settled surgical procedure that has been applied for centuries for medical requirements and religious purposes. The procedure that is applied in the known condition of the technique includes the cutting of the foreskin with the use of scissors and clamp and, then the approximation of the cut ends of the foreskin with the use of stitching materials.

Circumcision is a relatively short and inexpensive procedure in the modern operating rooms in the developed countries and, various surgical instruments have been developed to that end, but it still requires an operating room and a general or local anesthesia. Some of the inventions concerning the said apparatus and applications include: the invention "Sheath and retractable surgical tool combination", U.S. Pat. No. 4,491,132; "Disposable circumcision apparatus and method of use", U.S. Pat. No. 5,797,921; the invention "Circumcision device", U.S. Pat. No. 5,860,988; the invention "Circumcision device", U.S. Pat. No. 7,303,567; the invention "Surgical instrument", U.S. Pat. No. 7,591,824; and the invention "Circumcision apparatus and method using the same", publication no. US20060219753A1 from the United States of America.

Use of a central protection device inside the foreskin and of a ring outside the foreskin is the foundation for the following inventions from the United States of America that are applied in the known condition of the technique: "Surgical clamp" U.S. Pat. No. 3,111,124; "Circumcision instrument" U.S. Pat. No. 3,473,533; "Disposable circumcision device" U.S. Pat. No. 4,491,136; "Scavenge pump and accessory drive system" U.S. Pat. No. 3,520,632, "Circumcision device" U.S. Pat. No. 7,303,567, and "Atraumatic circumcision device and method to use same" U.S. Pat. No. 7,879,044.

The following patents, publications and inventions that are applied in the known condition of the technique have been tried, and it was identified that it was hard to cut the foreskin, the cosmetic results are not good, it takes about ten minutes or more to complete the circumcision procedure and, it requires anesthesia in the application thereof: the inventions from the United States of America: "Surgical clamp" U.S. Pat. No. 3,111,124; "Circumcision instrument" U.S. Pat. No. 3,473,533; "Disposable circumcision device" U.S. Pat. No. 4,491,136; "Scavenge pump and accessory drive system" U.S. Pat. No. 3,520,632; "Circumcision device" U.S. Pat. No. 7,303,567 and, "Atraumatic circumcision device and method to use same" U.S. Pat. No. 7,879,044: the publications from the United States of America: "Apparatus for performing circumcision", publication no. U.S. Pat. No. 6,660,012B2; "Clamp for performing circumcisions on newborns and a method of using the same", publication no. US20040215210A1 and US20060122626A1; "Novel implantable lead including sensor", publication no. US20080004681A1 and; "Circumcision clamp and surgical kit", publication no. US20080195116A1; and the publications from China: "Annular cutting anastomat for preputium penis", no. CN201119892Y and, "Posthetomy anastomat" no. CN201227313Y. Dislocation of the ring used in the said inventions causes bleeding, bad appearance, infection and irrigation due to foreign matter and, it may require a second visit to remove the device. Because of these reasons, these inventions are not commonly used.

The Mogen clamp, on which a simple modification is made in the bone cutting clamp in the US patent, "Circumcision clamp", registration no. U.S. Pat. No. 2,747,576A, is considered as not safe. However, use of the bone cutting clamp is easier than use of the Mogen clamp. There is a useful modification that allows us to close it tightly and, easily cut it from the upper side as it is in the bone cutter. A problem with use of the Mogen clamp is the possibility of the cutting of the urinary tract or a part of the penis head especially when it is used by inexperienced people. Bone cutting forceps are currently used by surgeons to ensure a fast, clean and safe circumcision, but it still requires the stitching of the wound and, the controlling of the bleeding. A cutting procedure with a laser or a diathermic knife could reduce the level of bleeding but, it may cause many problems, even disasters. As a result of this use, the burnt may spread the penis skin, gangrene may happen, and penis may need to be amputated. Classic surgical circumcision procedure currently used in a widespread manner requires local or general anesthesia, sterilized operating rooms and tools sterilized at high degrees and, thus is expensive and time-consuming (15-20 minutes), recovery takes too much time, a second visit is required to remove the stitches, and it causes many scars and irregular edges on the section where the stitches are.

SUMMARY

The disposable circumcision apparatus that is the subject of this invention contains two components that act in cooperation. These components are the modified bone cutting forceps and, the penis head protection probe. The purpose of developing the disposable circumcision apparatus and the method of use of this apparatus eliminates the disadvantages that exist in the known condition of the technique. The advantages of the apparatus that is subject of this invention, and the use thereof are as follows: the use of which allows that the circumcision procedure is completed in about one and half minute, which is very fast, and there is no bleeding during the procedure and operation, which does not require any anesthesia since the period in which the pain is felt is too short because the pain starts with the strong constriction effect of the bone cutter and ends within about ten seconds until the foreskin is removed, which does not require any dressing because the skin is attached to the mucosa and, that there is no open wound or hole, which ensures a very quick recovery since there is no gap between the mucosa and the foreskin due to the strong pressure that pushes the porous tissue and, makes the skin end closer to the end of the mucosa, that the infection possibility is very low due to there is no wound and, the procedure is constantly closed during the operation, that there is no risk of, in particular, viral transfection since the section but is subject to heating and, the apparatus is of disposable, that there is no need for second visit since there is no stitches or plastic ring, that no drug is needed other than a simple analgesia for the first day, that recovery is ensured in general with a small size of scar, that the cutting level is below the penis head level in respect of the skin and, above the penis head in respect of the mucosa, and thus the recovery line is away tram the penis head and, the attachment of the foreskin to the penis head, which is one of the complications of the circumcision, is prevented, that the wound is protected against the effect of possible erection since it is kept within a sensitive and expandable mucosa, that the level of edema and swelling, which may occur after the operation, is very low since the burnt skin fold is separated with the squeezed section and, thus toxic material is not transuded with normal skin and, a complete recovery is ensured within seven days.

After mass use of the apparatus that are applied in the known condition of the technique and, thousands of circumcision operations carried out, it has been identified that the circumcision apparatus and the method of use of thereof that is subject of this invention is not only superior to other methods but also is the best apparatus and method for use, in particular, in the circumcision operations carried out in remote locations, where high level of viral infection prevalence is expected, and African countries.

The most important advantage of this invention is that there will be no blood—even a single drop—seen in the process from the commencement to the completion of the operation. It takes only one person to use this disposable apparatus that is subject of this invention, therefore it is carried out without any assistant and, appropriate for people of all ages.

The structural and characteristic features and all the advantages of the invention will be more clearly understood due to the figures shown below and, the details referring to these figures and, thus the assessment should be made considering these figures and the details.

BRIEF DESCRIPTION OF THE FIGURES

FIG. 8a is a perspective view of the penis head protector

FIG. 8b is a cross section view of the penis head protector

LIST OF REFERENCE NUMBERS

Figure 1A:
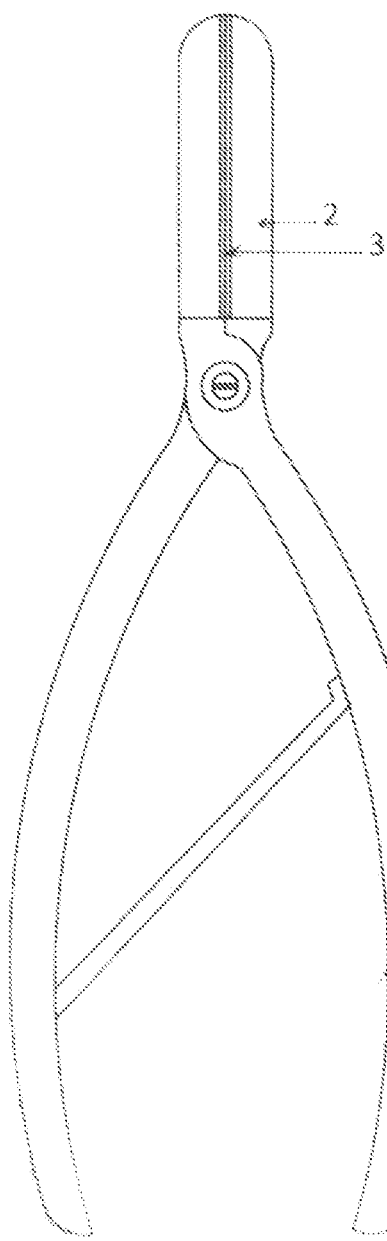
FIG. 1a is a top perspective view of the bone cutter, the closing line of which is modified.

1. Long handle
2. Cutting jaw
3. Closing line
4. Cutting sharp edge with mating 's' shape
5. Cylinder—a
6. Disposable part
7. Hollow area
8. Right and left parts
9. Penis head protection part
10. Handle
11. Contact point
12. Protrusion
13. Small hollow
14. Foreskin
15. Wing
16. Upper part
17. Cautery
18. Cylinder—b
19. Cylinder end
20. Penis
21. Penis head
22. Urinary tract opening
23. Coronal sulcus
24. Skin mark
25. Skin fold
27. Squeezed area
28. Clotted area
29. Foreskin mucosa

DETAILED DESCRIPTION

The disposable circumcision apparatus and the method of use of this apparatus are explained with use of the following references: long handle (1), cutting jaw (2), cutting line (3), cutting sharp edge with mating 's' shape (4) cylinder—a (5), disposable part (6), hollow area (7), right and left parts (8), penis head protection part (9), handle (10), contact point (11), protrusion (12), small hollow (13), foreskin (14), wing (15), upper part (16), cautery (17), cylinder—b (18), cylinder end (19), penis (20), penis head (21), urinary tract opening (22), coronal sulcus (23), skin mark (24), skin fold (25), squeezed area (27), clotted area (28) and foreskin mucosa (29).

The disposable circumcision apparatus and the method of use of this apparatus that is the subject of this invention contains two components that act in cooperation. These components are the modified bone cutting forceps and, the penis head protection part (9). The long handle (1) of the bone cutting forceps is suitable for providing high pressure. The matching surface of the jaw of the bone cutter is modified in such a manner that it has now a width of 1 mm instead of a sharp structure. There is a hollow in the shape of a triangle in 1 mm deep and 1.5 mm width from the upper surface of the closed jaw. At the end of the matching surface, there is a small protrusion (12) to prevent the foreskin (14) from being dislocated outside. The second component is the disposable penis head protection part (9) partially attached to the disposable part (6) and, this connection is established in such a manner that when the modified bone cutter's pressure is applied to the foreskin (14), the probe is separated from the cone, and leaves the penis head protection part (19) behind and, since the pressure could collect the mucosa loosely attached to the skin by means of a porous issue, the probe extents and, pushes the foreskin mucosa (29) in parallel with the skin.

While performing the circumcision with the disposable circumcision apparatus, first, the foreskin (14) is marked a few millimeters below the coronal sulcus (23) level and, the foreskin (14) is slowly retracted, and then disinfectant local anesthetic spray and, ointment as a lubricant are applied. The respective area should be smoothly cleaned since it may cause significant level of irritation and inflammation without any additional benefit The penis head protection part (9) is applied on the penis head (21), and then the foreskin is pulled to the probe above the cone, and then the foreskin is smoothly grasped with the probe and, pulled by the right hand. This painless maneuver is to adjust the length of the foreskin (14) that needs to be cut. Afterwards, the modified bone cutter is applied with the left hand starting from the skin mark (24), and the probe bottom end that lies forward and backward due to a slight pressure slides over the upper surface of the penis head protection part (9) and slightly moves above and, at the same time, it pushes the foreskin mucosa (29) ensuring that it is aligned with the foreskin (14) and, in this manner, the best cosmetic results are gained.

After the position of the bone cutter is checked, a firm pressure is applied and, this pressure pushes the porous tissue away from the pressure site and, makes the foreskin (14) closer to the foreskin mucosa (29) ensuring that the foreskin mucosa (29) and the foreskin (14) are strongly attached to each other. Most of the capillaries and small blood vessels will be dosed, but the large arteries will be able to be recanalized ten minutes after the bone cutter's pressure is removed. With use of the right hand, the foreskin (14) is cut by the cutting sharp edge on the surface of the bone cutter and, leaves a bone fold in the hollow of the bone cutter, the probe and the foreskin (14) is removed. An illuminated head in an oval shape pertaining to the stainless steel plated cup cylinder passes over the hollow, the heating is provided by gas or electricity, but the electric current should be cut off before the application. The temperature is between 140-300° C. The skin fold (25) is clotted making the foreskin (14) more attached to the foreskin mucosa (29) and, closes the arteries that may be recanalized. And then, the bone cutter pressure is removed and, slowly moves away from the penis (20).

A slight pressure that is applied to the penis head (21) from below pushes the penis head protection part (9) and, opens the cut site. The penis head protection part (9) is slowly taken out, another dosage of local anesthetic spray is applied and, there is no dressing other than a normal diaper. Another modification is used in the form of removable, disposable parts (6) of the bone cutter in order to prevent cross infection especially during the mass circumcision campaigns. The cutting jaw (2) is modified in such a manner it has cylinders—a (5) in parallel with each other, on which disposable parts are attached. The cutting jaw's (2) disposable parts (6) have as the same shape as the modified bone cutter and, this means that the matching surface, above of which there is a hollow when it is closed, has a width of 1 mm. The material of this disposable part (6) is a material that is sufficiently strong and resistant against high temperatures such as Bakelite or Catalin and, it also increases the protection against the heat transmission to the other foreskin (14) below it.

The last part is a cup cylinder—b (18) with an end in an oval shape covered by ceramic or stainless steel suitable for medical use. The cylinder—b (18) is routinely used in a simple arrangement with an electric operated soldering iron machine or a gas operated soldering iron machine. The electric soldering iron machine is directly plugged to the bottom end instead of a cable, thus it is not possible to operate it unless it is removed from the current.

FIG. 1a shows a bone cutter modified so that it has a longer handle (2) compared to a normal bone cutter so that more pressure may be applied to the circumcision apparatus cutting jaw (2). This cutting jaw (2) is longer than normal and has a modified cutting sharp edge with mating 's' shape (4) and, a blunt structure with a width of 1 mm. This means, when it is attempted to cut something, a skin mark (24) with a width of 1 mm instead of a cut when both jaws of this part (2) are closed. Within the framework of another modification, there is hollow with a width of 1.5 mm and with a depth of 1.5 mm on the closing line (3).

Figure 2:
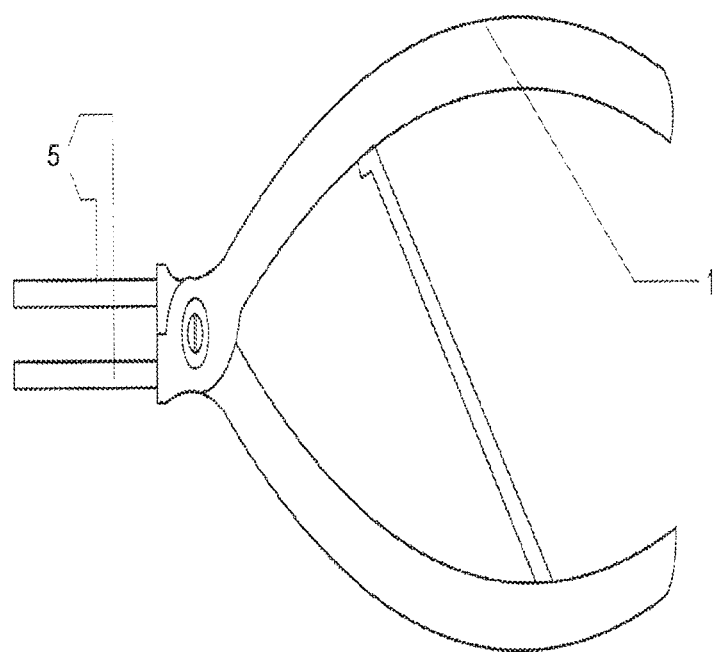
FIG. 2 is a top view of the bone cutter modified in such a manner that there are two cylinders in the cutting head.
Figure 3:
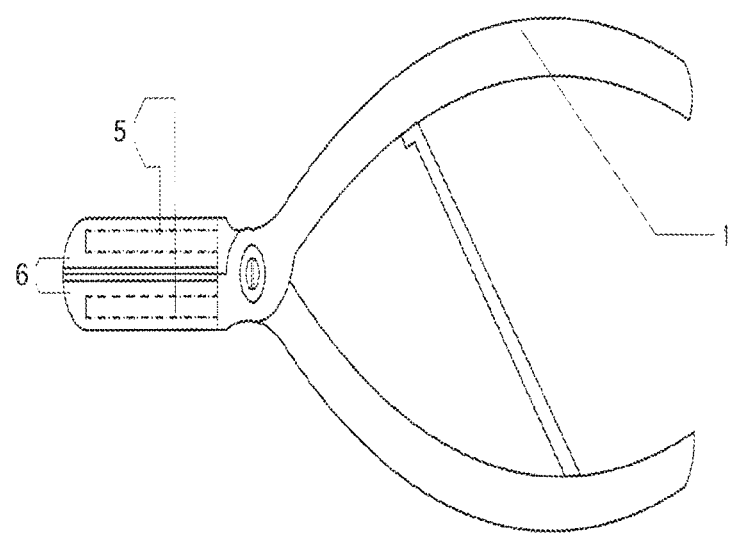
FIG. 3 is a top perspective view of the bone cutter with a disposable part attached.
Figure 4:
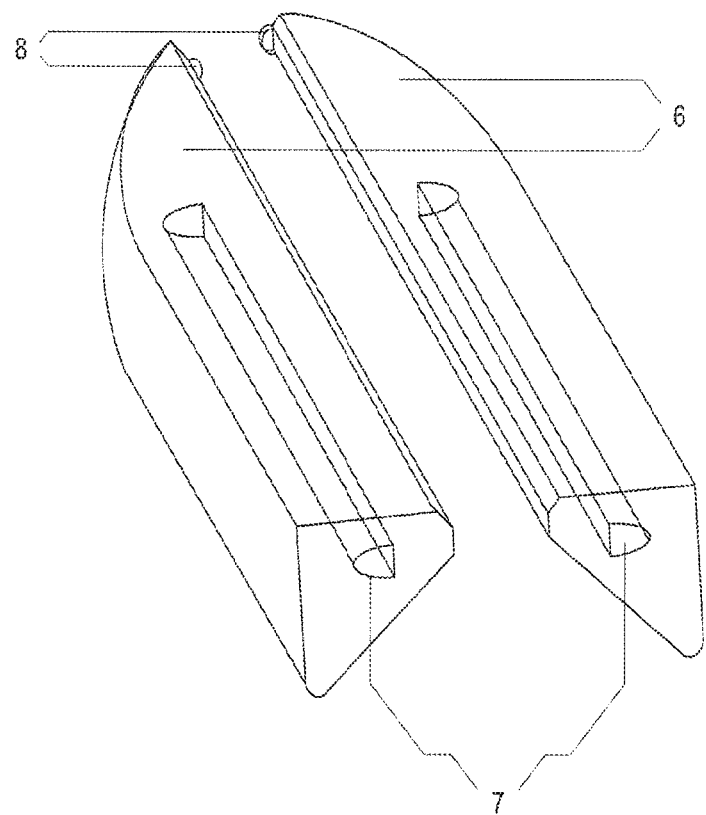
FIG. 4 is a perspective view of the disposable parts.

FIG. 2 shows tile modified bone cutter with a long handle (1) and, this is modified in such a manner that it has two cylinders—a (5) in parallel with each other when the clamp is tightly closed. The two disposable parts (6) attached on the cylinders—a (5) and a new clamp are arranged in such a manner that it has disposable parts (6) as is shown in FIG. 3. FIG. 4 shows the two disposable parts (6) separated from the clamp. There is a hollow area (13) in a special angled shape from inside and in a curved shape from outside, which fits the cylinder—a (5). There are the right and left parts (8) on the internal surfaces of the disposable parts (6), and there is a small protrusion (12) on the both sides at the end of the said right and left parts (8). The protrusions (12) are overlap each other when the cutting jaw (2) is closed and, there is a gap on the other side.

Figure 5:
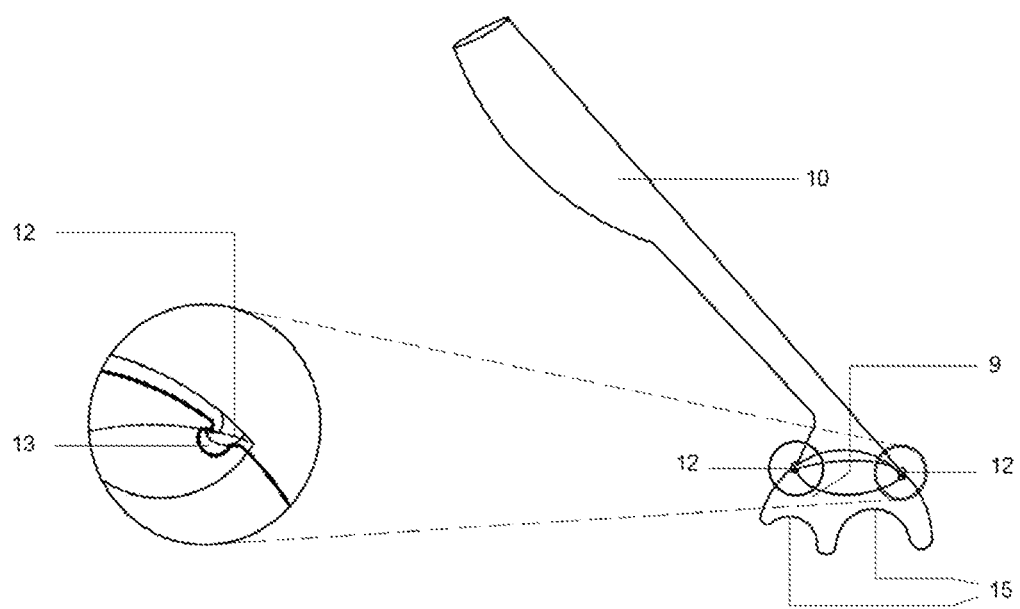
FIG. 5 is a perspective view of the the penis head protector.
Figure 6:
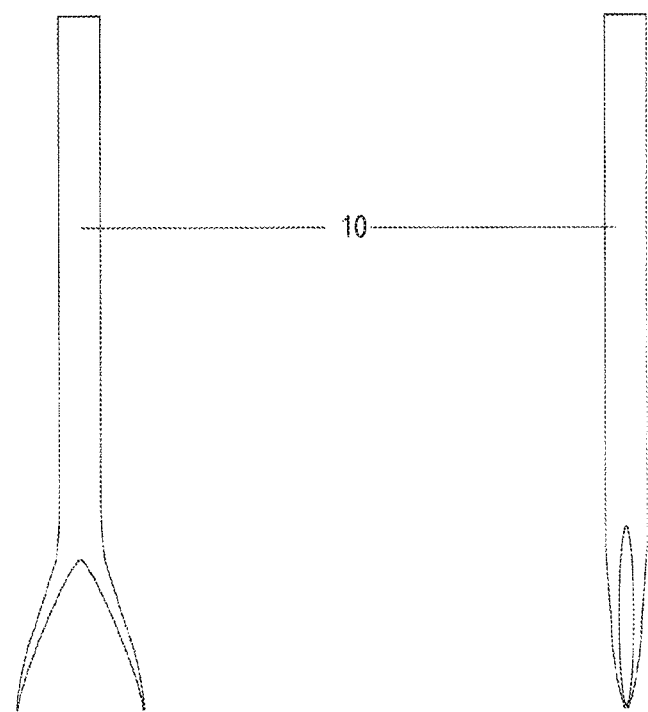
FIG. 6a is an anterior cross section of the normal shape of the penis head protector's handle.
FIG. 6b is an anterior cross section of the penis head protector when it is compressed from both sides by the modified bone cutter.
Figure 7:
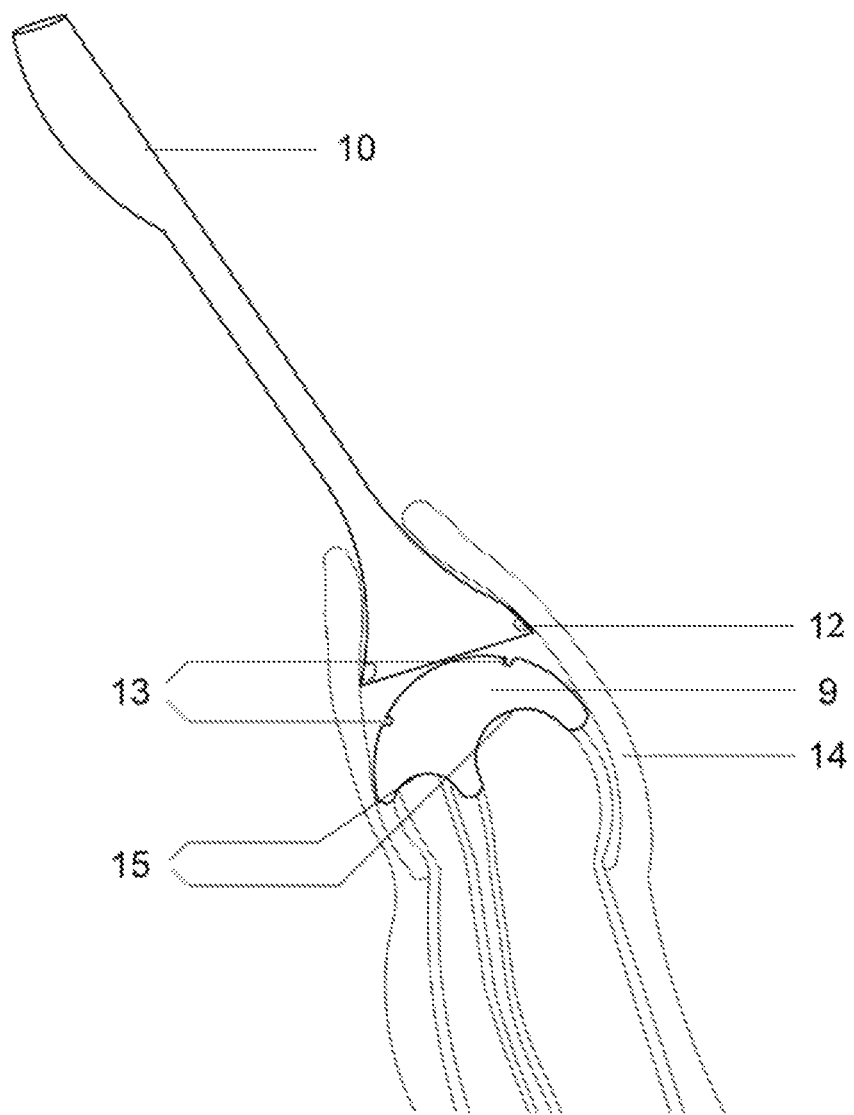
FIG. 7 is a cross section view of the penis head protector and its handle being inserted in the foreskin of the neonatal penis.

FIG. 5 shows the penis head protection part (9) with its handle (10). The contact point (11) has a small protrusion (12) on the end of the handle (10). The small gap on the penis head protection part (9) fits the small protrusions (12). In the normal position, the handle (10) will be completely open and, the distance between the protrusions (12) is slightly smaller than the distance between the hollows, so that the handle (10) protrusions (12) provide a small pressure to fix it to the penis head protection part (9) handle (10) as is shown in FIG. 6a. When the pressure pertaining to the modified bone cutter is applied on the both sides of the handle (10), the two wings (15) will be pressed against each other as is shown in FIG. 6b, and this will cause an increase in the distance between the two protrusions (12) sufficient to ensure their removal from the small hollow (13) as is shown in FIG. 7. This will ensure that the jaws push the foreskin (14) when pressure is applied from outside and, the bone cutter jaws extend according to their axis.

FIG. 8a shows the penis head protection part (9), the small hollows (13) and the wings (15) and, these wings (15) are thin and, adjustable to fit different sizes.

According to FIG. 8b that provides a sectional view at the wings (15) level, the wings (15) are thinner but, the upper part (16) is sufficiently thick to protect the penis head (21).

Figure 9A:
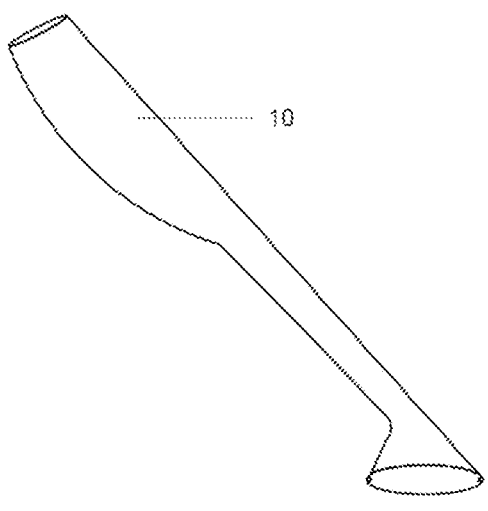
FIG. 9a is a perspective view of the penis head protector handle
Figure 9B:
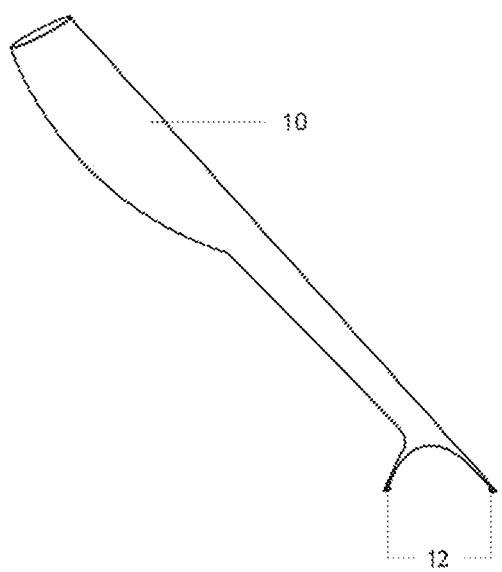
FIG. 9b is a cross section view of the penis head protector handle

FIG. 9a shows a perspective view of the handle (10), while FIG. 9b provides a section taken at the location of protrusions (12).

Figure 1B:
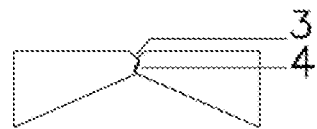
FIG. 1b is a cross-sectional view of the modified closing line of the bone cutter.
Figure 1C:
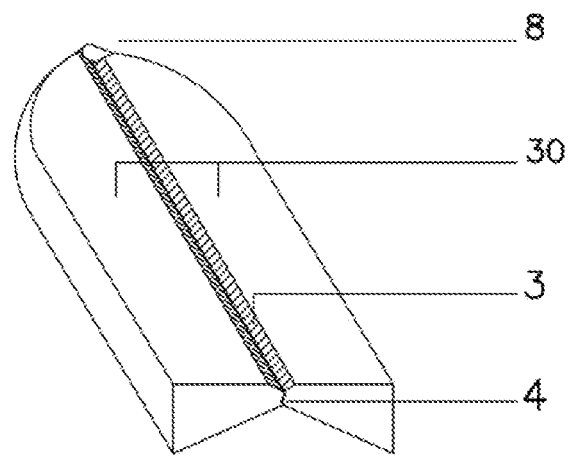
FIG. 1c is a perspective view of the jaws in a closed position.
Figure 10:
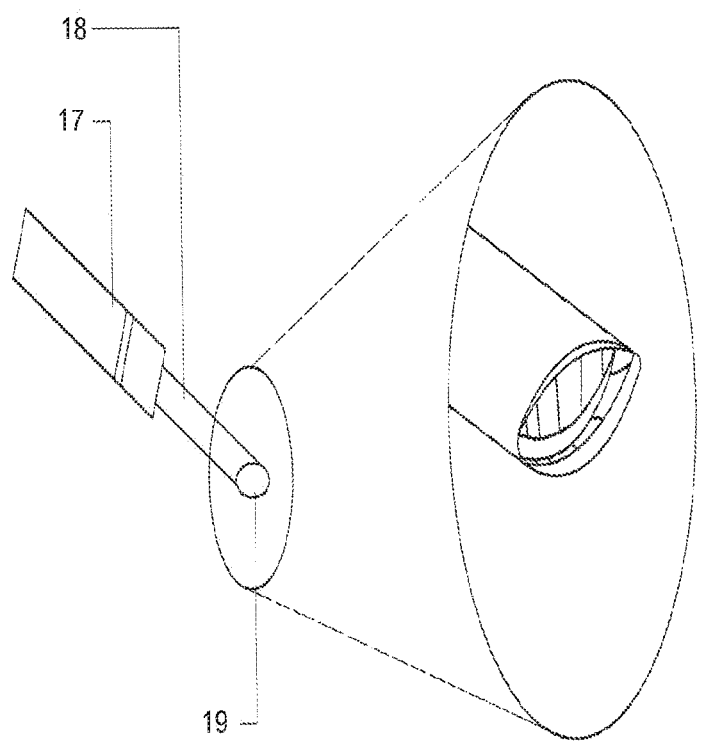
FIG. 10 shows the the cautery with a detailed view of the cylinder end

FIG. 10 shows the cautery (17) together with the cylinder—b (18) and, the cylinder end pertaining to the cautery (17) has an oval shape, and the extended section of this cylinder end (19) provides the full description of this shape and, a special attention is paid to ensure that it fits the closing line (3) in FIG. 1.

Figures 11A, 11B:
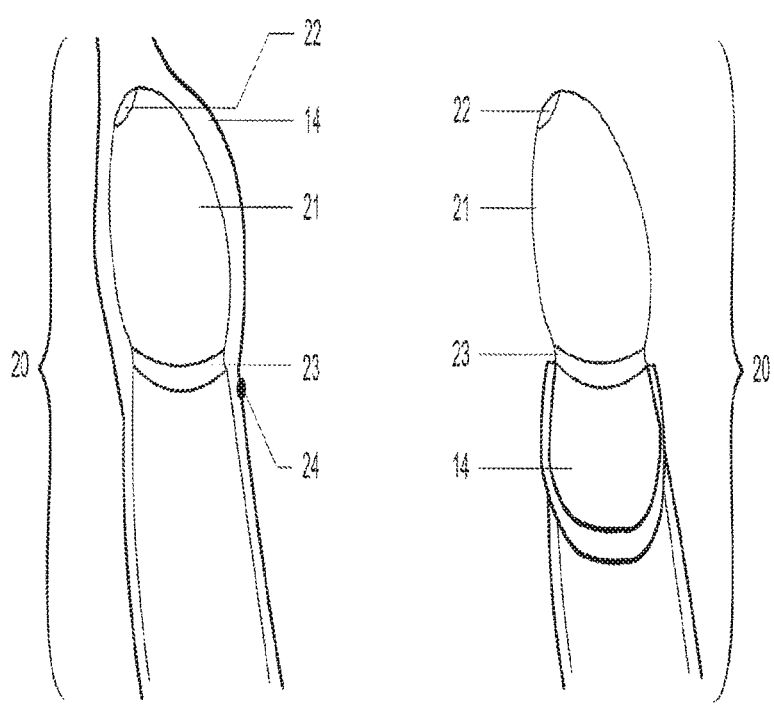
FIG. 11a shows the first step of the operation performed with the disposable circumcision apparatus
FIG. 11b shows the second step of the operation performed with the disposable circumcision apparatus

FIG. 11a shows the penis (20) and the foreskin (14), urinary tract openness (22) and the coronal sulcus (23) and, the penis head (21) and, there is skin mark (24) that indicates the bone cutter application level a few millimeters below the coronal sulcus (23) in a dropping position.

FIG. 11b shows the foreskin (14) retracted so that local anesthetic spray may be applied on the penis head (21) and, inside the foreskin (14).

Figures 11C, 11D:
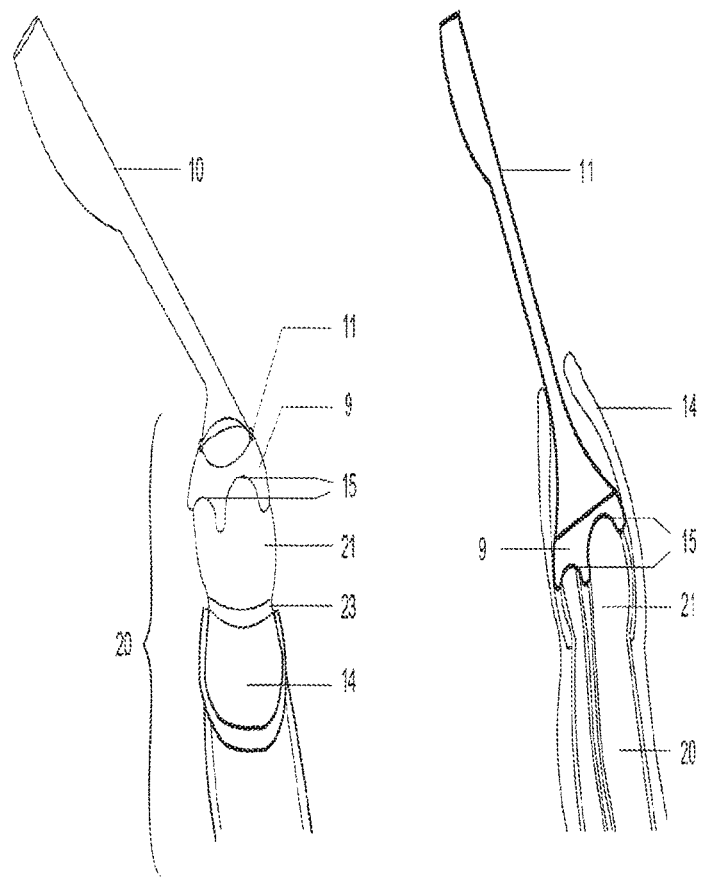
FIG. 11c shows the third step of the operation performed with the disposable circumcision apparatus
FIG. 11d shows the last step of the operation performed with the disposable circumcision apparatus

FIG. 11c shows the next step through which the penis head protection part (9) is applied on the penis head (21) after the antiseptic ointment is applied.

FIG. 11d shows the foreskin (14) being retracted in such a manner it reaches the handle (10).

Figure 12:
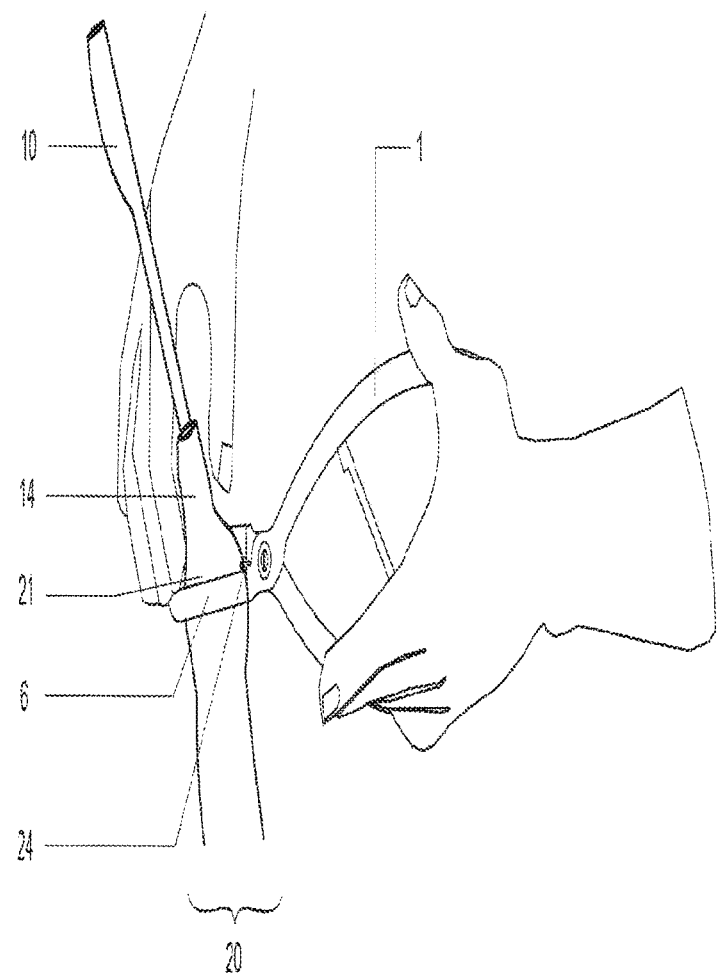
FIG. 12 shows use of the disposable circumcision apparatus by a surgeon

FIG. 12 shows the next step of the circumcision procedure, through which the surgeon grasps the foreskin (14) by means of the handle (10) using his right hand, and applies the modified bone cutter on the foreskin (14) starting from the skin mark (24) using his left hand.

Figure 13:
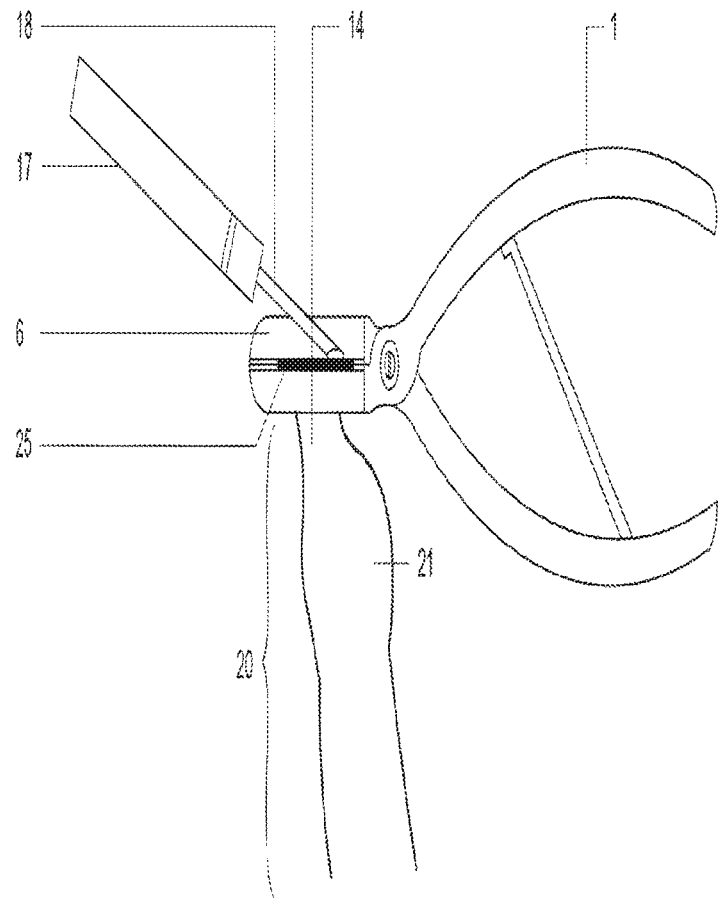
FIG. 13 shows the cautery passing the skin hold after the foreskin is cut

FIG. 13 shows the next step of the circumcision procedure, where foreskin (14) is already cut and, the skin fold (25) is visible on the closing line (3) and, the cautery (17) passes over the skin fold (25).

Figure 14:
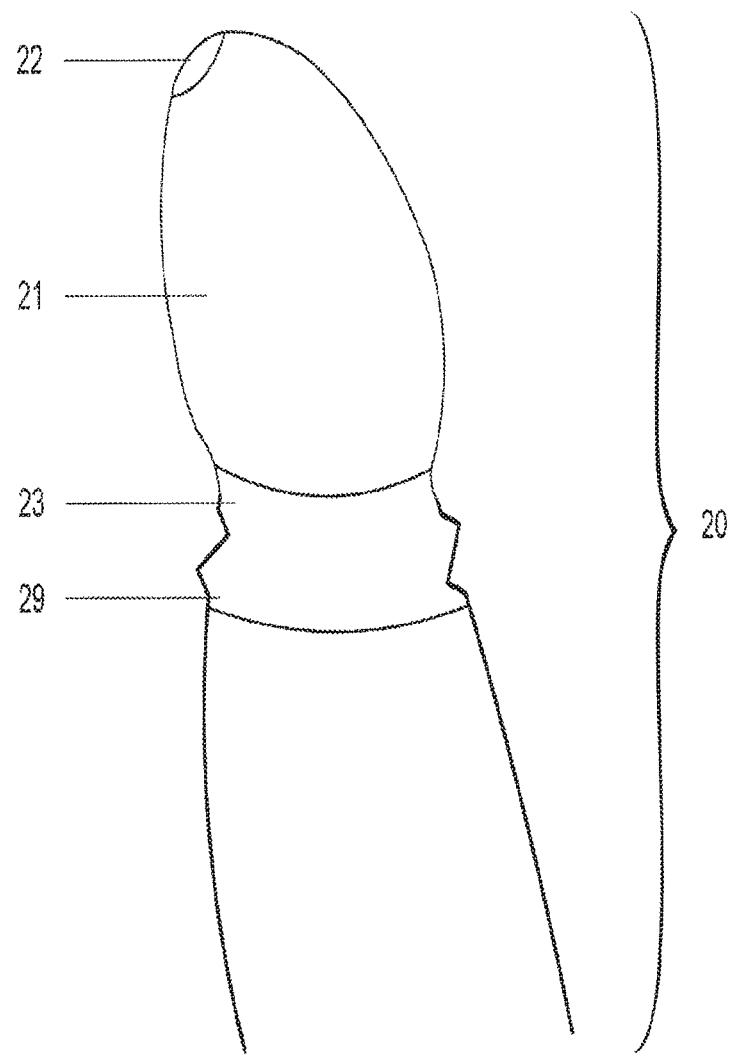
FIG. 14 shows the penis right after the circumcision

FIG. 14 shows the penis (20) after the circumcision and, the circumcision line is between the penis skin and the foreskin mucosa (29).

Figure 15:
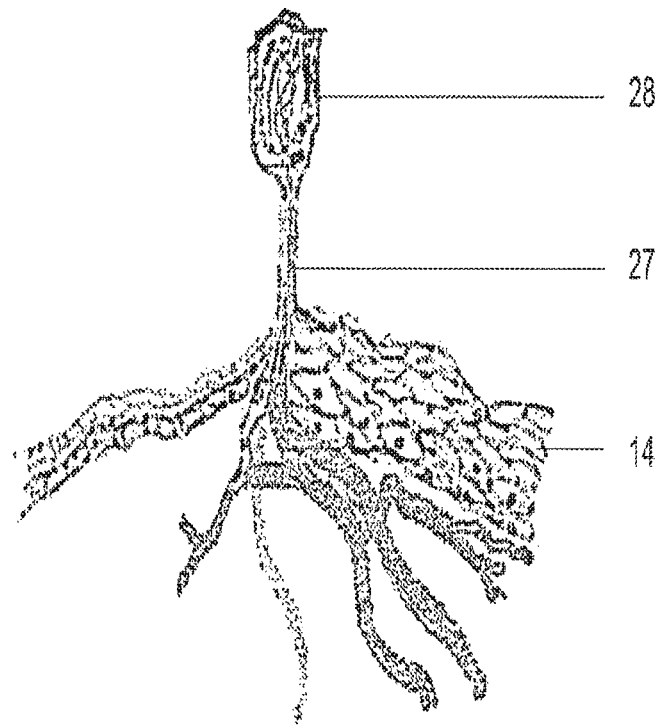
FIG. 15 is a microscopic cross-sectional view of the penis right after the circumcision

FIG. 15 is a diagram-style drawing for the microscopic section of the circumcision area and, it aims to show the squeezed area (27) and the clotted area (28). Here, it is possible to see how the blood vessels in the circumcision area are controlled.

The technical features and all other features mentioned in each claim are used only to facilitate the understanding of the claims, therefore it should not be considered that the procedure steps indicated by these reference numbers for the purpose of sampling limit the respective scope.

It is obvious that a person specialized about the technique may reveal the innovation specified in this invention by means of using similar structures and/or implements of this structure in other areas with similar purposes used in the respective technique. Therefore, it is also obvious that such structures would lack of innovation and, in particular, the criterion to exceed the known condition of the technique.

The invention claimed is:

1. A circumcision device comprising a circumcision clamp, a glans penis protecting piece, and a cautery cylinder,
    wherein the circumcision clamp comprises:
        a clamp with a handle having a predetermined length; and
        cutting jaws, wherein each of the cutting jaws has a mating surface with a width, wherein the mating surface has a mating 's' shape to prevent overlapping of the cutting jaws under very high pressure, each of the cutting jaws has a projection at an end of the cutting jaws,
    wherein when the cutting jaws are closed, a longitudinally extending channel is formed between upper surfaces of the cutting jaw and the projections of the cutting jaws from both sides come over each other and have a space for the opposite jaw to fit in.

2. The circumcision device of claim 1, wherein the width of each of the cutting jaws is 1 mm, the channel has a 1.5 mm width and a 1.5 mm depth from the upper surface of each of the cutting jaws above the mating surface and the projections, wherein a length of each of the projections is 1.5 mm,
    the circumcision clamp is one of medical grade stainless steel or disposable material, wherein when made from medical grade stainless steel, the circumcision clamp is sterilizable for re-use.

3. The circumcision device of claim 1, wherein the cutting jaws are metallic cylinders;
    wherein each of the metallic cylinders include a section curved from the outside and flat from the inside to insert into a disposable piece, wherein each of the disposable pieces has a hollow cavity to be inserted by the section of the metallic cylinder, wherein when the disposable pieces are fitted on the metallic cylinder, each of the disposable pieces has the projection with a length on each side of the disposable pieces, wherein when the disposable pieces are closed, the projection passes over each other, and wherein the disposable pieces are made of bakelite or catalin.

4. The circumcision device of claim 3, wherein the circumcision clamp is one of medical grade stainless steel or disposable material, wherein when made from medical grade stainless steel, the circumcision clamp is sterilizable for re-use.

* * * * *